(12) United States Patent
Kotte et al.

(10) Patent No.: US 9,736,977 B2
(45) Date of Patent: Aug. 22, 2017

(54) METHOD AND DEVICE FOR DISINFECTING POURABLE PRODUCTS, PREFERABLY SEEDS, WITH ACCELERATED ELECTRONS

(71) Applicant: EVONTA-Service GmbH, Radeberg (DE)

(72) Inventors: Mathias Kotte, Lohmen (DE); Olaf Roder, Dresden (DE)

(73) Assignee: EVONTA-Service GmbH, Radeberg (DE)

( * ) Notice: Subject to any disclaimer, the term of this patent is extended or adjusted under 35 U.S.C. 154(b) by 491 days.

(21) Appl. No.: 14/405,342

(22) PCT Filed: Jun. 3, 2013

(86) PCT No.: PCT/EP2013/061338
§ 371 (c)(1),
(2) Date: Dec. 3, 2014

(87) PCT Pub. No.: WO2013/182500
PCT Pub. Date: Dec. 12, 2013

(65) Prior Publication Data
US 2015/0216106 A1 Aug. 6, 2015

(30) Foreign Application Priority Data
Jun. 4, 2012 (DE) .................. 10 2012 209 434

(51) Int. Cl.
*A01C 1/08* (2006.01)
*A61L 2/08* (2006.01)

(52) U.S. Cl.
CPC ............. *A01C 1/08* (2013.01); *A61L 2/087* (2013.01)

(58) Field of Classification Search
CPC .................... A01C 1/08; A61L 2/087

USPC ............. 250/492.3, 453.11–455.11, 434
See application file for complete search history.

(56) References Cited

U.S. PATENT DOCUMENTS
5,801,387 A * 9/1998 Nablo ............... H01J 33/00
250/398

FOREIGN PATENT DOCUMENTS
DE 102006020483 A1 11/2007
EP 1080623 A1 3/2001

OTHER PUBLICATIONS
International Search Report issued in PCT/EP2013/061338, mailed Sep. 18, 2013.

* cited by examiner

Primary Examiner — Michael Maskell
(74) Attorney, Agent, or Firm — Heslin Rothenberg Farley & Mesiti P.C.

(57) ABSTRACT

The subject matter of the present invention is a method for treating pourable products made of particles which can be separated, preferably seeds (2), with accelerated electrons. During the method, a transparent product flow is guided, using gravity, in a product guiding channel (1) through the electron field generated by at least one electron accelerator (12) under low pressure or excess pressure. The product flow is guided by means of an accelerated gas flow (5) in such a way that the movement thereof corresponds in magnitude and direction to the accelerated movement, which the falling particles execute in said gas flow due to gravitational acceleration. In addition, a device is disclosed which realizes the acceleration of the gas flow (5) in the required way through the shaping of the product guiding channel (1).

29 Claims, 4 Drawing Sheets

Figure 1:
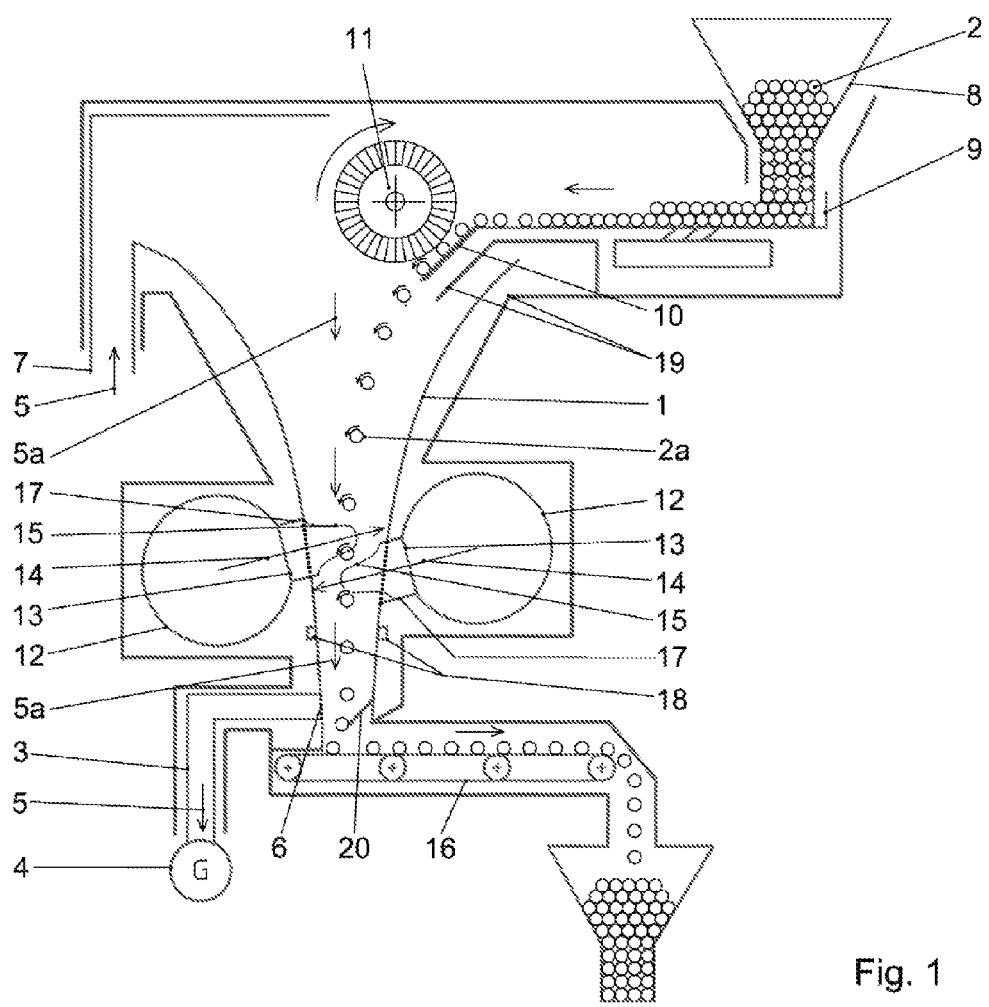

METHOD AND DEVICE FOR DISINFECTING POURABLE PRODUCTS, PREFERABLY SEEDS, WITH ACCELERATED ELECTRONS

CROSS REFERENCE TO RELATED APPLICATIONS

This application is a U.S. National Phase filing under 35 U.S.C. §371 of International Application No. PCT/EP2013/061338, filed Jun. 3, 2013, and published as WO 2013/182500-A1 on Dec. 12, 2013, which claims benefit of priority from German Patent Application Serial No. DE 102012209434.2, filed Jun. 4, 2012. The entire contents of each of the prior applications are incorporated herein by reference in their entirety.

The invention relates to a method and a device for disinfecting pourable products, preferably seed, with accelerated electrons. All granular products, that is bulk goods designated as powder or granulate, are understood under pourable, which products can be transported and separated in a continuous product flow. The preferred application area of the invention is the treatment of vegetation seeds or seed by killing or inactivating microorganisms and animal pests, which overwhelmingly colonize the surface as well as in and under the seed coat of the products or are conveyed separately with the product flow. Various methods and the corresponding devices for treating bulk goods with accelerated electrons are known.

Thus, methods are described, in which the bulk goods are loaded into a vacuum chamber and treated with electrons while falling (DD 291 704; DD 291 705; DD 291 677). By arranging one or more axial electron accelerators with in each case a beam scanned across the width of the curtain of bulk goods in the vacuum, a uniform exposure to electrons on all sides is supposed to be achieved. During the process control in the vacuum, all particles, regardless of the air resistance thereof, are, after a specified drop height, accelerated to the same speed by gravity, since there is no air friction. At the defined speed, each particle has the same exposure time in the electron beam. Thus, all particles receive the same electron dose.

A substantial deficiency of this method consists in that the generation and maintenance of the vacuum in the treatment chamber requires a very high evacuation expense. This is caused by the fact that air and water vapor are continuously carried into the treatment chamber with the bulk goods. A further deficiency is the arrangement of a plurality of product airlocks connected in series at the inlet and outlet of the vacuum chamber required for pressure graduation, which results in an enormous installation height of the entire system. The high costs for generating the vacuum, the required product airlocks, and the generation and scanning of the electron beam limit the application of the method to expensive specialty products.

In addition, devices are known, which use band emitters evacuated by pumps to generate the electron beam. The electrons arrive, via an electron exit window, also known as a beam exit port, out of the evacuated beam generation chamber of the beam emitter into a process chamber held below atmospheric pressure (D 4434 767 [sic: should read DE 44 34 767]; EP 07 05 531). The bulk goods fall within the process chamber in free fall in a gas atmosphere, usually air, through the electron field. Nozzles are arranged, which generate a gas flow at the electron exit window, to cool the electron exit window. Dust should also be kept away from the electron exit window by means of this cool gas flow.

A substantial deficiency of devices of this type, with process control under a gas atmosphere, consists in that the particles of the bulk goods are constantly accelerated in free fall due to the influence of the earth's gravity; however, a flow resistance operates in the treatment chamber due to the gas, which flow resistance decelerates the particles differently depending on the size, density, shape, and surface qualities thereof. Due to this, falling particles with a large ratio of surface to volume, such as husks, drop substantially slower than ball-shaped particles with small surfaces, such as grains. The resulting, often substantial, speed difference of different particles of the seed flow leads to quite varied exposure times to the electrons and thus to a broad scattering of the electron dose in the bulk goods flow. This has the result that particles, which receive a high electron dose, can be damaged, whereas the lethal dose required to kill the microorganisms and insects is not achieved on particles with a lower electron dose. Due to surviving organisms, a reinfection of the remaining particles due to propagation of the organisms can set in after treatment, which leads to an undesired infestation and thus to a loss of quality of the entire product volume.

With regard to the known devices, electron accelerators are used, which are arranged opposite each other. The disadvantage of an opposing arrangement consists in that the accelerated electrons, depending on their energy, can reach the electron exit window of the respectively opposing electron accelerator and can cause thermal damage due to increased energy input. An arrangement of this type limits the usable electron energy and the electron flow, and thus the achievable productivity and effectiveness of the device.

If the electron accelerators are arranged offset in height in order to avoid this disadvantage, this results in different distances to the overlying product supply. Since the particles are subject to constant acceleration during free fall, the speed thereof while passing by the upper electron exit window is lower than in the area of the lower-lying exit window, which can lead to the transmission of different energy doses. With regard to known devices (DE 44 34 767; EP 07 05 531), there exists the additional problem of speed differences in different particle shapes caused by air resistance. Contact of the particles with the bounding wall can additionally cause uncontrolled transverse and oscillating movements of individual particles. The result from the disadvantages listed is that particles on one side can receive a doubled dose, wherein only a reduced dose is transferred to the side facing away from the electron beam.

A further disadvantage of the solutions described consists in that the gas flow for cooling the electron exit window leads to a reduction of the static pressure between the electron exit window and the bulk goods flow due to the speed-related dynamic pressure of the gas flow. The pressure equalization resulting therefrom results in a gas flow from the treatment zone in the direction of the electron exit window, which pressure equalization pulls light-weight particles, such as dust or hulls, with it. Particles, which are larger than the mesh width of the protective grid between the product flow and the electron exit window, remain hanging there, successively clog the grid, and lead to an undesired reduction of the electron transparency of the grid. In contrast, smaller particles can enter the electron exit window through the mesh of the protective grid and lead to a reduction of the lifespan of the sensitive film of the electron exit window due to abrasion.

An additional deficiency consists in that the band emitters used to maintain the high vacuum in the acceleration chamber must be constantly evacuated. The high-vacuum pumps required for this purpose necessitate high operating and maintenance expenses and limit the economics of the method.

Additional methods and devices for treating bulk goods are known, in which the required energy dose is achieved by multiple passes through the electron field. The homogeneity of the treatment is supposed to be increased by this means (EP 10 80 623). A substantial disadvantage of this method is that X-rays generated in the treatment chamber by the effects of the electrons generate an X-ray dose within the volume of each bulk particle, which dose is added to during each pass through. In the application to living products, such as seeds, this increased X-ray dose influences the embryo in the interior of the seed and can lead to undesired genetic alterations of the seed and thus to substantial losses in quality.

The underlying problem of the invention is to create a method and an associated device, which enable treating pourable products, independent of the size distribution of the particles as well as the density, shape, and surface qualities thereof, without evacuating the treatment chamber, with great homogeneity of the energy input at the individual particles and at the entire surface thereof, such that the electron dose required to safely kill microorganisms and insects is achieved on each surface element, and a reduction in quality or genetic change of the product due to an electron dose that is too high and/or due to an X-ray dose that is too high is avoided. It is in particular the goal to kill damaging microorganisms and insects, which colonize the surface and an edge layer of the particles up to a depth of approx. 500 μm, by treatment with accelerated low-energy electrons.

The problem is inventively solved by the method according to claim 1. The subject matter of claim 13 is a device suitable for implementing the method. Particularly advantageous embodiments are described in claims 2 to 12 and 13 to 29.

According to the inventive method, the flow of pourable product is initially transported by means of a conveying device into a treatment chamber, wherein preferably a mechanical separation of the particles already takes place. This has the advantage, that even at high product throughput, the particles are sufficiently separated and are supplied to the treatment chamber with negligible overlap. The treatment chamber as well as the areas of the product supply and discharge are shielded against the emission of X-rays. The product supply and discharge takes place using suitable conveying devices, such as vibration conveyor channels, high-speed belts, or rotary feeders. In combination with a tailored X-ray protective housing, this enables a continuous material flow while simultaneously preventing the emission of X-ray radiation.

Upon entry of the particles into the product guiding channel, generally directed vertically downwards, a continuous acceleration of the particles takes place due to the effect of gravity. By this means, the translation speed v of the particles constantly increases according to the law of physics $$v=\sqrt{2*g*h} \qquad (1)$$

where g is the gravitational force of the earth and h is the drop path traveled by the particle. The product guiding channel is connected to a gas conveying device, preferably a gas blower, which generates a constant gas volume flow within the product guiding channel in the direction of drop of the product flow. A particle flow guided vertically downward in the gas volume flow in the transport direction is formed. Due to the gas conveying device, either an excess pressure is generated above the product guiding channel or a low pressure is generated at the lower end of the product guiding channel, which affects the gas movement in the direction of drop. The excess or low pressure is not so large that special airlocks or pressure resistant measures are necessary; however, it represents a significant deviation from the atmospheric pressure. The pressure buildup is possible in particular because the supply or discharge devices for the product represent a significant flow resistance to the inflowing or outflowing air.

In a preferred embodiment, air is sucked in at the upper end of the product guiding channel and introduced into the same. The air is expelled at the lower end. For this purpose, gas conveying devices are located at the lower and/or upper ends of the product guiding channel. By using a gas conveying device, which is arranged at the upper end of the product guiding channel, a low pressure prevails in the interior of the treatment chamber. If the gas conveying device is arranged at the lower end of the product guiding channel, then the gas is sucked in from said channel and an excess pressure prevails. If a gas conveying device is provided at the lower and upper ends of the product guiding channel, then an excess pressure prevails in the upper part of the product guiding channel, and a low pressure in the lower part. At the points, where the gas or air exits from the product guiding channel, the associated openings are advantageously provided with devices that prevent the exit of the product. These are preferably grids, sieves, gauze, or perforated metal plates, preferably in connection with associated cleaning devices. In the gas flow guided toward the outside, in a preferred embodiment, an ozone catalytic converter is arranged upstream of the exhaust into the environment, which ozone catalytic converter reduces ozone arising from oxygen in the treatment zone and preferably removes it to an acceptable level.

It is further preferred that the gas flow from the gas conveying device is fed in a circuit, in that the gas flow is guided at the lower end of the product guiding channel back to the upper end thereof. The gas conveying device is preferably arranged between the exhaust of the gas flow at the lower end of the product guiding channel and the supply at the upper end. A particularly preferred embodiment provides a cleaning device for the redirected gas flow. This cleaning device removes dust from the gas flow and prevents the accumulation thereof in the circulating gas flow. The cleaning device is thereby preferably designed as a filter (bag filter), cyclone, or a similar device according to the prior art. The discharge of the gas flow is preferably sealed against the suctioning in or exhausting of larger particles by a protective grid, which can be preferably automatically or manually cleaned. Gas losses, which result from the exit via the product supply or discharge, are compensated for, depending on the type of gas in the gas flow, as needed, by additional gas conveying devices, by a supplemental supply from a gas tank, or from the atmosphere using suction devices.

A further preferred embodiment provides a plurality of gas conveying devices, which are arranged at the lower and/or upper ends of the product guiding channel.

The gas flow is formed preferably by air, nitrogen, or carbon dioxide. Inert gases, which do not introduce unintended chemical reactions with the products, are preferred. A particularly preferred embodiment provides the addition of treatment gases, which cause intended chemical or biological reactions in or on the particles.

The cross section of the product guiding channel constantly decreases toward the bottom in the direction of drop of the product flow. Due to a cross section of the product guiding channel configured in such a way, the gas flow is accelerated at approximately the same rate as the product flow, by which means the speed of the surrounding gas largely corresponds at each point with the speed of the particles accelerated in the drop. The product flow is guided by means of an accelerated gas flow, the movement thereof corresponding in magnitude and direction to the accelerated movement, which the falling particles execute in said gas flow due to gravitational acceleration. Air friction, as this occurs in known solutions in gas atmospheres, is thus excluded or is at least negligible, and all particles of a bulk goods flow have approximately an identical speed. This has the advantage that pourable products, independent of the composition as well as the type, shape, or size of the particles, are guided at a defined speed through the treatment zone of the electrons, and, in this way, a homogeneous electron dose is applied to all particles.

After or directly upon leaving the conveying device to the product supply or upon entrance into the product guiding channel, the individual particles receive, in a preferred embodiment, a pulse that leads to a rotational movement. The rotational axis of the particles runs thereby preferably parallel to the longest extension of the electron accelerator. The particles retain this rotational movement during the dwell time in a product guiding channel and during the effect of the electrons in the area of the treatment zone. In particular during the use of only one electron accelerator, this brings along the advantage that the electrons affecting the particles from one preferred direction can reach the entire surface across the circumference of the particles, and a further improvement of the homogeneity of the electron dose is achieved, without necessitating expensive measures for reflecting or diverting the accelerated electrons. The necessity for multiple treatments can also be dispensed with, since the required homogeneity and the level of the energy dose are achieved in one pass through. By this means, an increased productivity is achieved in comparison to known methods, and the described risks of loss of quality of the product due to X-ray doses that are too high, which can occur during multiple treatments, can be excluded.

This rotational movement is e.g. realized via rolling off of an incline, or by a brush or roller type of device, which transfers a rotation to the particles in the moment of leaving the conveying device.

The cross section of the product guiding channel is rectangular in a preferred embodiment. In the area of the effective zone of the electrons, the cross section has two opposing longer sides and two opposing shorter sides. The reduction of the cross section is achieved in that the two opposing longer sides approach each other in conjunction with the drop path of the particles. The two short sides run preferably parallel. The product flow pours downward as a transparent "curtain", preferably centered between the longer sides of the cross section, preferably across the entire length. In this context, a transparent curtain means that the mutual covering of the falling particles is as low as possible, when seen from the longer sides of the cross section, whereas the particles have advantageously as small a lateral distance to each other as is possible.

The gap width s between the two opposing longer sides of the product guiding channel constantly decreases in the direction of drop of the product flow in this embodiment, and said gap width is preferably configured such that it follows the correlation $$s = k * \frac{1}{\sqrt{h}} \qquad (2)$$

where h is the drop path traveled by the particle, and k is a constant that lies between 170 mm$^{3/2}$ and 250 mm$^{3/2}$.

A further preferred embodiment provides an annularly configured gap, which likewise narrows in conjunction with the drop height traveled. The product supply takes place in this case above a center column that is surrounded by the annular gap. It is further preferred that the product supply takes place through the center column, e.g. by means of a screw conveyor. In a preferred embodiment, the screw is equipped with an elastic edge or with elastic bristles. The product exits at the upper end of the center column and falls over the edge into the annular gap. In a preferred embodiment, a rotational movement is also imparted to the particles in this case, which movement the particles retain in the drop. This takes place, by way of example, via an intake section at the edge of the center column, across which section the particles roll downwards, and thereby incur a rotational movement.

After a certain drop height (preferably between 20% and 80%, particularly preferably between 30% and 70%, and most particularly preferably between 40% and 60% of the total drop height), the particles reach the treatment zone. One or more electron accelerators are arranged here laterally on the product guiding channel. The electron accelerators are adapted in the shape thereof to the product guiding channel and emit electrons preferably across the entire width of the product flow. In particular, in the case of a rectangular product guiding channel, one or more electron accelerators extending linearly are used, which accelerators extend with the longitudinal axis parallel to the longer side of the cross section and transverse to the direction of drop. If two or more electron accelerators are used in a device, then the electron stream required can be advantageously adapted exactly to the speed of the particles and the gas flow at the corresponding drop height h, by which means a constant dose is transmitted at this point. The energy of the electrons lies preferably in a range of 50 keV to 500 keV, and particularly preferably in the range from 70 keV to 300 keV, and more particularly preferably in the range from 80 keV to 200 keV.

Uncontrolled transverse and oscillating movements of individual particles, as can arise using known methods and devices, are preferably reduced due to the reduction of friction at the product guiding channel by using fluidically optimized means. The inventive method enables the combination of decisive advantages of an inexpensive process control at conditions below or above atmospheric pressure and using homogeneous transmission of the electron dose at any particle size and shape in the product flow with an improved effectiveness in the combat against microorganisms and insects. Since the process is not carried out in vacuum, the substantial expense related to vacuum technology is omitted.

The electron accelerator(s) typically function(s) under vacuum conditions. A preferred embodiment provides for the provision of encapsulated electron accelerators, in which the electron flow exits via windows that comprise a material particularly highly permeable for electrons, which material, however, preserves the vacuum conditions in the respective electron accelerator. Due to a preferred special encapsulation of the electron accelerators by means of solder or weld connections, the high-vacuum pumps usually required for the permanent maintenance of vacuum within the acceleration chamber are omitted. Thus, vacuum pumps can be advantageously dispensed with. By using one or more hermetically encapsulated electron accelerators, the economics of the method are substantially increased in comparison to the known solutions.

The inventive method includes the described active gas guidance within the product guiding channel. Due to the speed of this constantly accelerated gas flow and the dynamic pressure resulting therefrom, the static pressure is lowered in the product guiding channel. The product guiding channel is opened in the area of the electron exit window for the passage of the electrons into the treatment zone of the product guiding channel. As protection from the exit of product out of the product guiding channel, the opening or openings are, in a preferred embodiment, realized by a flat perforation of the channel wall or are covered using a narrow mesh gauze or a grid. In a preferred embodiment, gas, preferably air, can flow into the product guiding channel through these openings, since the reduced static pressure in the product guiding channel can lead to a bypass gas flow, which is directed from the electron exit window in the direction of the product guiding channel. The inflowing gas is guided over the electron exit window, by which means said window is convectively cooled. In order to set the pressure relationships within the product guiding channel, the inflowing gas can be supported by means of a separate auxiliary blower in an embodiment. An advantage of this cooling consists in that the bypass gas flow directed into the product guiding channel keeps the perforated area, or area covered by means of grids, through which the accelerated electrons are guided into the treatment zone, free from deposits. By this means, the otherwise additional means for generating cooling gas by means of large blowers, are omitted in this embodiment, which offers further economic advantages.

Due to the active gas guidance in the product guiding channel and due to the bypass gas flow into the channel, a reduction of friction between the particles of the product flow and the walls is affected in this area. This can also be used for targeted friction reduction in other partial areas of the product guiding channel. By this means, transverse and oscillating movements of individual particles are minimized, which leads to an additional improvement in the dose homogeneity. The bypass gas flow is preferably diverted from the gas flow circulating in the circuit, which is moved by the gas conveying device. The design based on pressure technologies ensures that the bypass gas flow enters in the necessary amount. An associated control is advantageously carried out by means of known devices (dampers, sliders, etc.).

Preferably, at least one pressure sensor is arranged in the product guiding channel. A plurality of pressure sensors are particularly preferably distributed across the height of the product guiding channel. In a preferred embodiment, the entire system is controlled by means of an electronic data processing unit. The pressure sensors and the further sensors (by way of example sensors for electron flow density and dose measuring devices for X-ray radiation, temperature sensors on the electron accelerators, sensors for measuring the product flow, etc.) advantageously likewise transmit the data detected to the data processing unit. The transmission can take place by wire or wirelessly. The data processing unit then advantageously controls the product flow by means of the conveying devices as well as the at least one electron accelerator and the one or more gas conveying devices.

Setting the method parameters (electron flow, acceleration voltage, type of gas, gas pressure) takes place with regard to seed based on morphological features (seed coat thickness and density, position of the embryo, type of seed). By means of the known calculation methods for determining the penetration depth of accelerated electrons in the material, the necessary process conditions can thus be calculated. This takes place preferably in the data processing unit or previously, wherein the necessary information is then input into the data processing unit prior to the start of the process.

A further preferred embodiment provides the arrangement of two or more electron accelerators. In order to prevent a mutual thermal influence on the electron accelerators, which preferably are located opposite each other, said accelerators are arranged offset in height and the output is adjusted to the respective speed of the product flow. A further advantageous variant is the arrangement of opposing electron accelerators at a rotation around the horizontal longitudinal axis in an angle range of 5° to 45°, such that the average speed vector of the electrons to the speed vector of the particle flow deviates by this angle from the orthogonal. This arrangement can also be selected for offset electron accelerators and enables high electron flows for achieving high energy doses at improved homogeneity of the energy input on the particles of the product flow.

In a further preferred embodiment, means for fire and explosion protection are provided. In particular, spark detectors are used, which do not react to the wave length of daylight or to the (luminous) gas plasma generated by the electrons in the effective zone.

The inventive device is suitable for additional pourable products in addition to the use for disinfection or sterilization of bulk seeds. These are, by way of example, pharmaceutical products, like tablets, granulates, capsules, as well as all types of contaminated pourable masses, e.g. dirt, plastic waste (shredded), recyclables, etc.

The invention will be described in more detail by means of one embodiment. The associated figures show:

FIG. 1: A section through a device for disinfection of seeds using a fluidically optimized shape for the product guiding channel and gas blower, a hermetically encapsulated electron accelerator with electron exit window and protective grid, as well as product supply using a vibration conveying device, rotational device for the particles, product discharge, and an integrated X-ray protection device, FIG. 2: A section through a part of the device according to FIG. 1 in the area of the product guiding channel with gas guidance and bypass flow to keep the grid in the product guiding channel clear and for cooling the electron exit window, FIG. 3: A section through a part of the device according to FIG. 1 in the area of the rotational device for the particles, FIG. 4: A section through a part of the device according to FIG. 1 in the area of the measuring device for determining the electron flow density.

FIG. 1 represents the basic structure of the exemplary device with product guiding channel 1, which has a constantly decreasing gap width in the direction of drop of the seed particles 2a. In the lower area, the product channel 1 is connected to a gas blower 4 via a suction line 3, which blower constantly supplies a gas flow 5 toward the outside. Due to this constant exhaust, a low pressure is generated in the inside of the treatment chamber. To protect against the exhaust of seed particles 2a, a grid 6 is arranged at the inlet to the suction line 3. An inflow nozzle 7 for supplying the gas flow 5 is located in the upper area of the product guiding channel 1. Air, carbon dioxide, or nitrogen is used as the process gas. The defined decreasing gap width of the product guiding channel 1 in the direction of drop causes a constant acceleration of the gas 5*a* within the product guiding channel 1 in the same measure as the acceleration due to gravity affecting the seed particle 2*a*.

The bulk seed 2 is supplied to the process via a buffer container 8. A metering device (not depicted) is located at the outlet of the buffer container 8, which metering device limits the volume flow of the seed 2 to a defined level. The bulk seed 2 arrives at a vibration conveying device 9, which induces a constant feed and pre-separation. The vibration device 9 has, within the product guiding channel 1, an angled segment 10 with a roughened surface to increase friction. A rotating brush roller 11 forms an adjustable gap with the segment 10, the diameter of said gap corresponds to the bulk seed particle 2*a*. Due to the rotational movement of the brush roller 11, the particles of seed 2 rolling off the segment 10 receive a rotational pulse before they transition into the drop at constant acceleration due to gravity.

Electron accelerators 12 are arranged on two sides of the product guiding channel 1. The flat electron beam 14 generated by the electron accelerators 12 enters through the electron exit window 13 into the product guiding channel 1 and moves in the direction of the seed particle 2*a* while forming a Gauss-shaped intensity profile 15 in the plane of representation, which profile has a half-power width of approximately 30 mm. In the Z-axis, perpendicular to the plane of representation, the electron beam 14 has a dimension of approximately 1000 mm. The electron beam 14 is further scattered during the propagation thereof in the air and affects the falling and rotating seed particle 2*a*, supplied to the gas flow 5*a*, diffusely and from all sides. After exposure to the electron beam 14, the bulk seed exits the product guiding channel 1 via a high-speed belt 16 arranged directly thereunder within less than one second, by which means the exposure to X-ray radiation is reduced to a minimum.

The electron accelerators 12 are arranged rotated around the longitudinal axes (Z-axis) thereof, such that the primary movement direction of the electron beam 14 is not at a right angle to the movement direction of the seed particle 2*a*. By this means, the respectively opposing electron accelerator 12 is not hit, and also high electron energies and electron flows cannot damage the opposing electron exit window. Measuring devices 17 in the form of molybdenum plates for recording a measuring signal depending on the electron flow distribution are arranged on the product guiding channel 1 next to the electron exit windows 13.

An optical measuring system 18 enables the measurement of the density of the seed particle 2*a* and the determination of the product state.

The entire system is equipped with an X-ray protective housing 19, which prevents the emission of X-ray radiation into the environment. Due to the design with the integration of the vibration conveying device 9, the high-speed belt 16, and the interior barriers 19, the exposure time of the seed particle 2*a* in the area of the X-ray radiation is reduced to a minimum.

Figure 2:
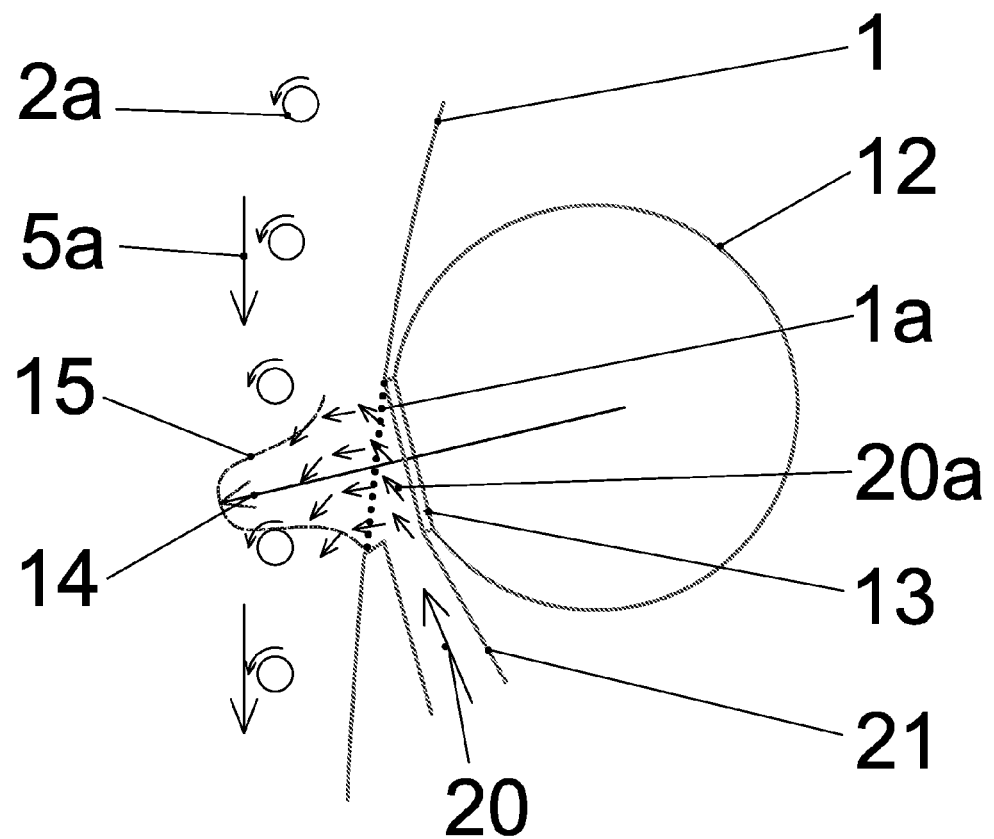

FIG. 2 is a section through a part of the device according to FIG. 1, with the right side of the product guiding channel 1 and an electron accelerator 12 represented as enlarged, but only schematically. This area is the effective zone of the electron beam, in which the actual disinfection takes place. The electron beam 14 is guided using the Gauss-shaped intensity distributor 15 through the perforated region 1*a* into the product guiding channel 1 and affects the rotating seed particle 2*a* on all sides. The static low pressure generated by the gas flow 5*a* causes a gas flow 20, which is directed from outside through the perforated area 1*a* into the product guiding channel 1 and keeps said perforated area clear of contamination and particles. A flow channel 21 induces the targeted inflow of air with a selected direction distinctly parallel to the electron exit window 13 and cooling the same through convection.

Figure 3:
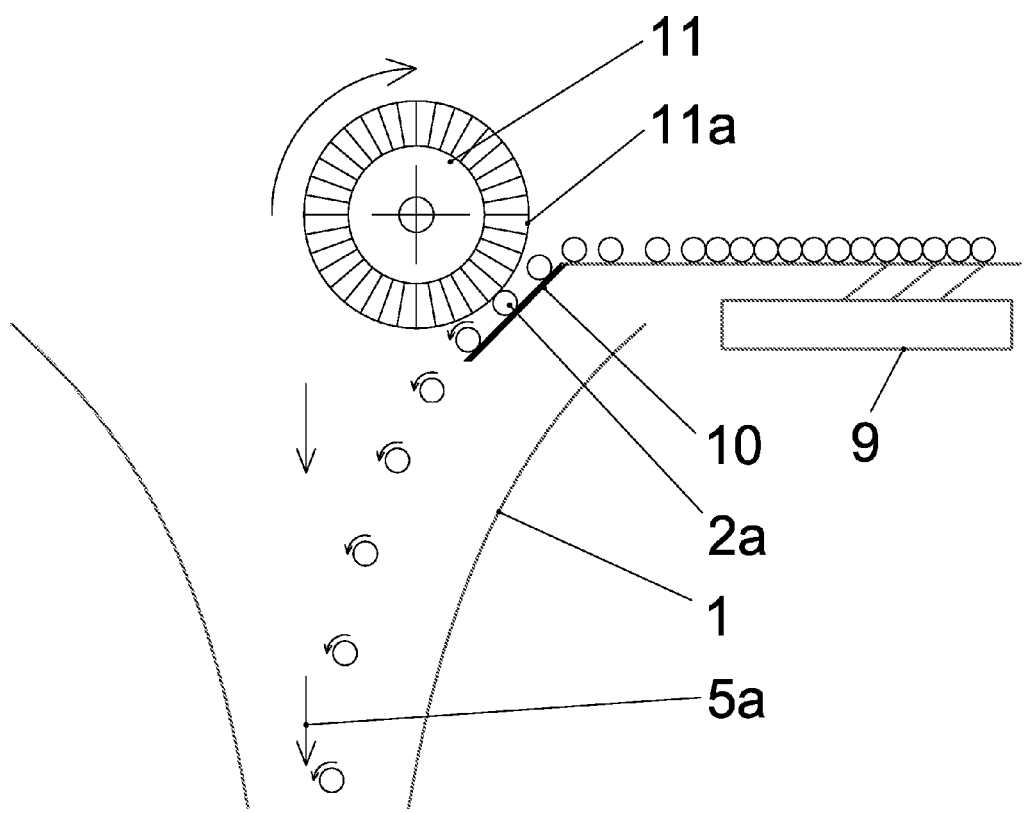
Figure 4:
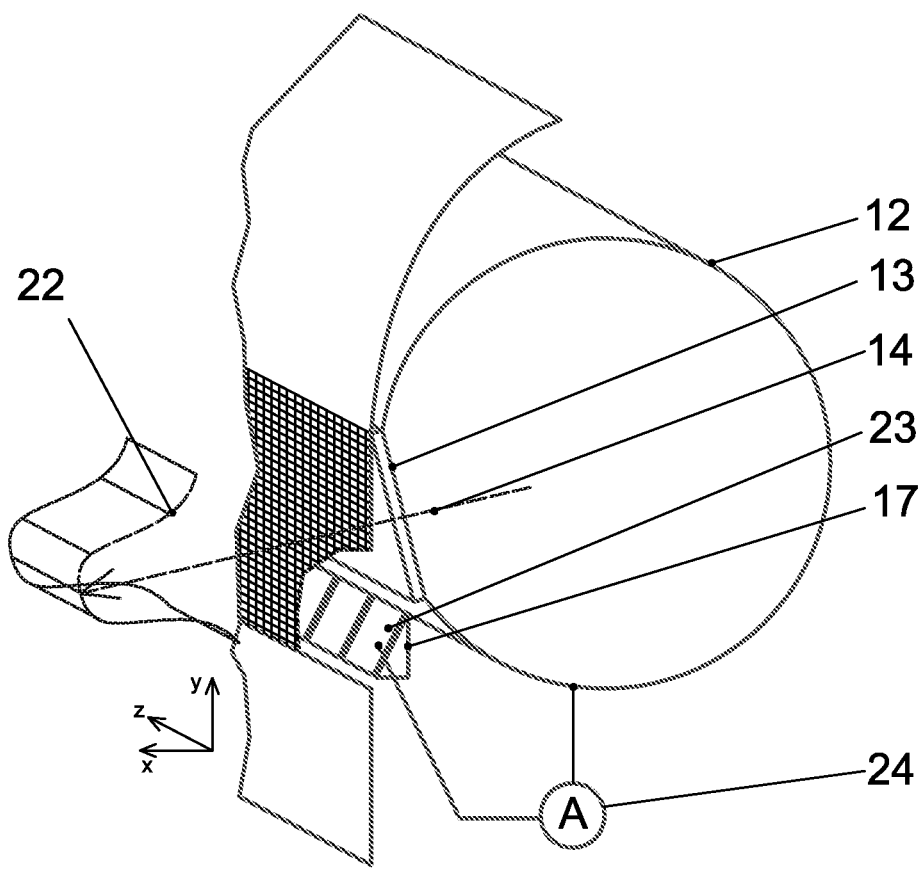

FIG. 3 shows an enlarged schematic section through a part of the device according to FIG. 1 with the rotational device for the seed particle 2*a*. The rotating brush roller 11 captures the seed particle 2*a* and transfers it to the rough surface of the segment 10 of the vibration conveying device 9 in a rotational movement. Kernel size differences are compensated for by the elastic bristles 11*a*, such that after leaving the rotational device, all seed particles 2*a* rotate.

In the device, which is schematically represented in FIG. 4, a measuring device 17 is arranged on the side of the electron exit window 13, which measuring device determines the electron flow distribution 22 present in the Z-axis of the plane of representation. Said device comprises several temperature resistant molybdenum plates 23 positioned in the area of the edge electrons of the electron beam. The molybdenum plates are coupled to the potential of the housing of the electron accelerator 12 via electrical conductors. A measuring device 24 connected in series serves to detect the outgoing electron flow.

LIST OF REFERENCES

1 Product guiding channel
1*a* Perforated area of the product guiding channel
2 Bulk seed, seed (product)
2*a* Seed particle
3 Suction line
4 Gas blower
5 Gas flow
5*a* Gas flow in the direction of drop
6 Grid
7 Inflow nozzle
8 Buffer container
9 Vibration conveying device
10 Angled segment
11 Brush roller
11*a* Elastic bristles of the brush roller
12 Electron accelerator
13 Electron exit window
14 Electron beam
15 Intensity distribution of the electron beam
16 High speed belt
17 Measuring device for electron flow distribution
18 Optical measuring system
19 X-ray protective housing
20 Incoming gas flow
20*a* Incoming gas flow for cooling the electron exit window
21 Flow channel
22 Electron flow density distribution
23 Molybdenum plate
24 Measuring device

What is claimed is:

1. A method for treating pourable products made of particles which can be separated, preferably seeds, with accelerated electrons, during which a transparent product flow is guided, using gravity, in a product guiding channel through the electron field generated by at least one electron accelerator under low pressure or excess pressure, characterized in that the product guiding channel has a decreasing cross section in the movement direction of the particles, and the product flow is guided by means of an accelerated gas flow, the movement thereof corresponding in magnitude and direction to the accelerated movement, which the falling particles execute in said gas flow due to gravitational acceleration.

2. The method according to claim 1, characterized in that the acceleration of the gas flow takes place through suction at the outlet and/or through injection at the inlet of the product guiding channel, which narrows in the transport direction.

3. The method according to claim 1, characterized in that the particles are imparted with a rotational movement prior to or at the entrance into the product guiding channel.

4. The method according to claim 3, characterized in that the imparting of the rotational movement of the particles takes place by rolling off of a slanted surface.

5. The method according to claim 3, characterized in that the imparting of the rotational movement of the particles takes place via short-term simultaneous contact with at least one fixed and one rotating component.

6. The method according to claim 3, characterized in that the initiation of the rotational movement of the particles takes place via simultaneous contact with components rotating at different speeds.

7. The method according to claim 1, characterized in that to reduce friction at least in partial areas of the product guiding channel, a gas flow with a movement component directed 45° to 90° to the movement direction of the product flow is introduced into the product flow.

8. The method according to claim 1, characterized in that a process gas is supplied during the treatment of the pourable product using accelerated electrons.

9. The method according to claim 8, characterized in that air or nitrogen or carbon dioxide is used as the process gas.

10. The method according to claim 1, characterized in that the process gas is guided in a circuit.

11. Method The method according to claim 10, characterized in that the process gas is subjected to dedusting.

12. The method according to claim 1, characterized in that the product guiding channel has a narrowing, rectangular cross section according to the correlation $$s = k * \frac{1}{\sqrt{h}},$$

where s is the gap width between two opposing sides of the product guiding channel, h is the drop path traveled by the particle, and k is a constant that preferably has a value between 170 mm$^{3/2}$ and 250 mm$^{3/2}$.

13. A device for disinfecting a product flow of pourable particles, preferably seed, with accelerated electrons, having:
    a process chamber filled with gas with a vertical product guiding channel for guiding the product flow,
    means for airlock-free, isolating guiding of pourable particles to the upper end of the product guiding channel,
    at least one electron accelerator with an electron exit window and the associated high voltage and control systems,
        which is arranged laterally on the product guiding channel,
        the electron beams of which hit the product flow guided through the product guiding channel and thus form a treatment zone, wherein
        the emission width of the electron accelerator corresponds at least to the width of the product flow,
    means for airlock-free exhaust of the product flow,
    means for generating a low pressure or excess pressure in the process chamber,
    characterized in that
    the product channel has a cross section constantly narrowing in the movement direction of the particles,
    the means for generating a low pressure or excess pressure in the process chamber, and the design of the particle guiding channel induce a constant volume flow of gas in the product guiding channel, which generates an accelerated movement of the gas identical to the movement of the particles in magnitude and direction.

14. The device according to claim 13, characterized in that the product guiding channel has a rectangular cross section and is curved over the course thereof on at least one of the two longer opposing sides such that the cross section thereof decreases in the transport direction.

15. The device according to claim 13, characterized in that a device for generating a rotational movement of the particles of the product flow is arranged prior to or across the treatment zone.

16. The device according to claim 14, characterized in that the gap width s between the two longer opposing sides of the product guiding channel follows the correlation $$s = k * \frac{1}{\sqrt{h}}$$

in relation to the drop height h of the particles, where s is the gap width between two opposing sides of the product guiding channel, h is the drop path traveled by the particle, and k is a constant that preferably has a value between 170 mm$^{3/2}$ and 250 mm$^{3/2}$.

17. The device according to claim 13, characterized in that the electron accelerator is a flat beam generator with a hermetically-sealed, evacuated acceleration chamber, for which operation no vacuum pumps are necessary.

18. The device according to claim 13, characterized in that the product guiding channel has a perforation in the area of the electron exit window, which perforation enables a gas flow in the direction of the product flow to keep dust clear as well as for the entry of the electrons into the product guiding channel and the influence thereof on the product.

19. The device according to claim 13, characterized in that the means for generating the low pressure or excess pressure are gas conveying devices.

20. The device according to claim 19, characterized in that the means for generating the low pressure or excess pressure convey the gas of the treatment chamber in a circuit.

21. The device according to claim 20, characterized in that a dedusting device is arranged in the conveying circuit.

22. The device according to claim 13, characterized in that a measuring device for detecting the electron beam density is arranged between the product guiding channel and the electron exit window, and/or in the product guiding channel.

23. The device according to claim 22, characterized in that the measuring device comprises at least two metal segments arranged electrically insulated, which segments are coupled to the ground potential via electrical conductors, and a measuring device for detecting the outgoing electron flow is interconnected to the electrical conductor in order to generate a signal depending on the electron flow density.

24. The device according to claim 13, characterized in that a measuring device for detecting the product status is arranged at the passage area of the electrons in the product guiding channel.

25. The device according to claim 24, characterized in that the measuring device comprises at least two metal segments electrically insulated from each other and from the walls of the product guiding channel, which segments deliver a signal depending on the particle flow density by means of a test voltage prevailing between the segments.

26. The device according to claim 24, characterized in that the measuring device is an optical system, which delivers a signal depending on the particle flow density.

27. The device according to claim 13, characterized in that a vibration conveying device equipped with an X-ray protection device is arranged for supplying the product.

28. The device according to claim 13, characterized in that a conveying device equipped with an X-ray protection device is arranged for supplying the product.

29. The device according to claim 13, characterized in that an ozone catalytic converter is connected upstream of the gas flow guided outward into the environment by the exhaust.

\* \* \* \* \*

UNITED STATES PATENT AND TRADEMARK OFFICE
CERTIFICATE OF CORRECTION

PATENT NO. : 9,736,977 B2  
APPLICATION NO. : 14/405342  
DATED : August 22, 2017  
INVENTOR(S) : Mathias Kotte and Olaf Roder Page 1 of 1

It is certified that error appears in the above-identified patent and that said Letters Patent is hereby corrected as shown below:

In the Claims

Column 11, Line 40, Claim 11: Delete "Method"

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*